(12) United States Patent
Higazi

(10) Patent No.: US 8,507,436 B2
(45) Date of Patent: Aug. 13, 2013

(54) PEPTIDES DERIVED FROM PLASMINOGEN ACTIVATOR INHIBITOR-1 AND USES THEREOF

(75) Inventor: Abd Al-Roof Higazi, Mobile Post Shimshon (IL)

(73) Assignee: D-Pharm Ltd., Rehovot (IL)

( * ) Notice: Subject to any disclaimer, the term of this patent is extended or adjusted under 35 U.S.C. 154(b) by 599 days.

(21) Appl. No.: 12/670,099

(22) PCT Filed: Jul. 24, 2008

(86) PCT No.: PCT/IL2008/001027
§ 371 (c)(1),
(2), (4) Date: Apr. 30, 2010

(87) PCT Pub. No.: WO2009/013753
PCT Pub. Date: Jan. 29, 2009

(65) Prior Publication Data
US 2010/0215636 A1    Aug. 26, 2010

Related U.S. Application Data

(60) Provisional application No. 60/951,485, filed on Jul. 24, 2007.

(51) Int. Cl.
*A61K 38/49* (2006.01)

(52) U.S. Cl.
USPC ....... 514/14.5; 514/14.6; 514/14.7; 514/14.9; 530/300

(58) Field of Classification Search
None
See application file for complete search history.

(56) References Cited

U.S. PATENT DOCUMENTS

2003/0211095 A1* 11/2003 Higazi ............... 424/94.64
2006/0069035 A1   3/2006 Higazi ............... 514/17

FOREIGN PATENT DOCUMENTS

| WO | WO 99/20295 | 4/1999 |
| WO | WO 02/34776 | 5/2002 |
| WO | WO 03/006042 | 1/2003 |
| WO | WO 03/095476 | 11/2003 |
| WO | WO 2008/018084 | 2/2008 |

OTHER PUBLICATIONS

Nassar et al., Blood; 2004; 103: 897-902.*
Schellinger et al., Crit Care Med 2001; 29: 1812-1818.*
Akkawi, Sa'ed et al., (2006) LRP and $\alpha_v \beta_3$ Mediate tPA Activation of Smooth Muscle Cells, Am J Physiol Heart Circ Physiol. 291, H1351-H1359.
Armstead, William M. et al., (2004) Altered NO function contributes to impairment of uPA and tPA cerebrovasodilation after brain injury; Journal of Neurotrauma 21, 1204-1211.
Armstead, William M. et al., (2005) Plasminogen activators contribute to age-dependent impairment of NMDA cerebrovasodilation after brain injury; Developmental Brain Research, 156(2):139-146.
Armstead, William M. et al., (2006) Neutralizing the neurotoxic effects of exogenous and endogenous tPA; Nature Neuroscience 9(9):1150-1155.
Atochin, D.N. et al., (2004) Mouse model of microembolic stroke and reperfusion Stroke, European Journal of Pharmacology 35, 2177-2182.
Bdeir, Khalil et al., Urokinase Mediates Fibrinolysis in the Pulmonary Microvasculature (2000) Blood 96:1820-1826.
Ding-Zhou, L. et al., (2002) L-NAME reduces infarction, neurological deficit and blood-brain barrier disruption following cerebral ischemia in mice. European Journal of Pharmacology 457(2-3):137-146.
Gennarelli, Thomas A. (1994) Animate models of human head injury;Journal of Neurotrauma 11(4):357-368.
Abdulla, H., Abdullah et al., (2000) Urokinase-derived peptides regulate vascular smooth muscle contraction in vitro and in vivo. FASEB J. 14:1411-1422 (2000).
Joslin, Gregg et al., (1993) Cross-Competition for binding of binding of alpha 1 -antitrypsin (alpha1 AT)-elastase complexes to the serpin-enzyme complex receptor by other serpin-enzyme complexes and by proteolytically modified alpha1 AT. The Journal of Biological Chemistry vol. 268(3):1886-1893.
Korkmaz, Brice et al., (2002) Discriminating between the activities of human neutrophil elastase and proteinase 3 using serpin-derived fluorogenic substrates. J Biol Chem 277(42):39074-39081.
Nassar, Taher et al., In Vitro and In Vivo Effects of tPA and PAI-1 on Blood Vessel Tone (2004) Blood 103(3):897-902.
International Search Report PCT/IL2008/001027 mailed Oct. 15, 2008.

\* cited by examiner

*Primary Examiner* — Bridget E Bunner
*Assistant Examiner* — Christina Borgeest
(74) *Attorney, Agent, or Firm* — Winston & Strawn LLP

(57) ABSTRACT

The present invention relates to isolated 18-mer peptides corresponding to amino acid residues 369-386 of human plasminogen activator inhibitor 1 (PAI-1) and fragments thereof, compositions that include such peptides, and uses of such compositions for treating thromboembolic diseases and pathological conditions associated with neurological damage.

19 Claims, 7 Drawing Sheets

US 8,507,436 B2

PEPTIDES DERIVED FROM PLASMINOGEN ACTIVATOR INHIBITOR-1 AND USES THEREOF

This application is a 371 filing of International Patent Application PCT/IL2008/001027 filed Jul. 24, 2008, which claims the benefit of application No. 60/951,485 filed Jul. 24, 2007.

FIELD OF THE INVENTION

The present invention relates to peptides derived from human plasminogen activator inhibitor 1 (PAI-1), compositions comprising same, and uses thereof for treating thromboembolic diseases and pathological conditions associated with neurological damage.

BACKGROUND OF THE INVENTION

Approximately 750,000 patients develop ischemic stroke in the US annually, of which about 150,000 of the incidents are fatal. Notwithstanding more than 50 years of effort (Zivin, J. A. 1999. Neurology 53, 14-19), the thrombolytic agent, tissue-type plasminogen activator (tPA) remains the only FDA-approved treatment for acute stroke. However, its brief therapeutic window and the high incidence of post-treatment complications including intracranial hemorrhage (ICH) has limited the clinical use of tPA to approximately 3% of all patients presenting with symptoms of stroke (Lapchak, P. A. 2002. Curr Neurol Neurosci Rep. 2, 1-6; Nagai, N. et al. 2001. Blood 97, 3086-3092). Preventing the adverse effects of tPA on the central nervous system (CNS) is likely to enhance the benefits of treatment and provide new approaches to ameliorate the impact of stroke.

The deleterious effects of tPA may not be related exclusively to its proteolytic activity. The inventor of the present invention and co-workers have previously reported that exogenous tPA decreases cerebral vascular resistance in rats (Nassar, T. et al. 2004. Blood 103, 897-902) and piglets (Armstead, W. M. et al. 2004. J Neurotrauma 21, 1204-1211); that the levels of tPA in the CNS are elevated after fluid percussion brain injury (FPI), which is thought to mimic concussive traumatic brain injury (Gennarrelli, T. A. 1994. J Neurotrauma 11, 357-368); and that administration of tPA at the examined concentrations induces cerebral vasodilation in naïve animals (Nassar, T. et al. 2004, supra; Armstead, W. M. et al. 2004, supra; Armstead, W. et al. 2005. Develop Brain Res, 156, 139-146).

International Patent Application Publication No. WO 03/006042 to the inventor of the present invention discloses a six amino acid peptide derived from plasminogen activator-1 (PAI-1) having the amino acid sequence EEIIMD which is capable of reducing the undesirable side effects such as intracerebral hemorrhage induced by fibrinolytic agents, e.g., tPA, uPA, tcuPA, streptokinase, rt-PA or alteplase, rt-PA derivatives or anisoylated streptokinase complex. In the protocol disclosed, the peptide was introduced into the thrombolytic regimen in later stages to prevent the vasoactive or side effects of the primary fibrinolytic agent. It was further reported that PAI-1 and the PAI-1 derived peptide EEIIMD inhibit tPA-mediated signal transduction (Akkawi, S. et al. 2006. Am J Physiol Heart Circ Physiol. 291, H1351-1359) without compromising its catalytic activity.

International Patent Application Publication No. WO 03/095476 to the inventor of the present invention teaches administration of the peptide EEIIMD of SEQ ID NO: 11, or the peptide acetyl-RMAPEEIIMDRPFLYVVR-amide of SEQ ID NO: 2, anti-LRP antibodies or LRP antagonists, in combination with one or more fibrinolytic agents for enhancing the fibrinolytic activity, reducing the side effects due to vasoactivity caused by the fibrinolytic agents, and/or prolonging the half lives of the fibrinolytic agents. That invention further relates to combination compositions and/or therapy regimens comprising the polypeptide EEIIMD of SEQ ID NO: 11 and/or the Ac-RMAPEEIIMDRPFLYVVR-amide peptide of SEQ ID NO: 2 and one or more currently used plasminogen activators.

U.S. Patent Application Publication No. US2006/0069035 to the inventor of the present invention discloses that the EEIIMD of SEQ ID NO: 11 peptide reduces the effective dosage of a thrombolytic agent required in the prevention or treatment of thromboembolic disorders. This in turn reduces the risk for side effects of the thrombolytic agents, the side effects being manifested in the late stage of therapy.

International Application Publication No. WO 2008/018084 to Higazi and Cines discloses the use of the peptide EEIIMD of SEQ ID NO: 11 and 6-mer peptide analogs thereof in preventing neuronal damage and in treating brain injury.

There is still an unmet need for improved, highly effective means for treating thromboembolic disorders, particularly those related to ischemic stroke, and neurological diseases.

SUMMARY OF THE INVENTION

The present invention provides isolated peptides consisting of 18 amino acid residues corresponding to the amino acid segment 369-386 of human PAI-1 and fragments thereof which consist of 7 to 17 amino acid residues comprising the sequence EEIIMD of SEQ ID NO: 11. The peptides are particularly useful for treating neurological damage associated with exogenous and/or endogenous tissue-type plasminogen activator (tPA).

It is now disclosed for the first time that an 18-mer peptide having the amino acid sequence $R_1$-Arg-Met-Ala-Pro-Glu-Glu-Ile-Ile-Met-Asp-Arg-Pro-Phe-Leu-Phe-Val-Val-Arg-$R_2$ (SEQ ID NO:1) corresponding to the segment 369-386 of human PAI-1 and certain analogs and fragments thereof including a known 18-mer peptide analog having the amino acid sequence acetyl-RMAPEEIIMDRPFLYVVR-amide (SEQ ID NO:2) have neuroprotective activity.

The present invention discloses that the 18-mer peptides are highly effective in reducing tPA-induced brain edema and tPA-induced intracranial bleeding in animal models in which brain injury has been caused. The 18-mer peptides are also very effective in reducing tPA-induced mortality after mechanical stroke in an animal model. The 18-mer peptides of the present invention are found to exert higher neuroprotective activity than that of a 6-mer peptide of the amino acid sequence Glu-Glu-Ile-Ile-Met-Asp (SEQ ID NO:11).

Unexpectedly, the peptides of the present invention block the deleterious effects associated with both exogenously administered tPA and endogenous tPA. Moreover, the efficacy of the 18-mer peptides of the present invention to block the deleterious effects associated with endogenous tPA is found to be higher than that exerted by the known 6-mer peptide. Thus, the extent of brain infarct, intracerebral hemorrhage, edema, and mortality, whether induced by exogenous and/or endogenous tPA can be reduced or even abolished by the peptides of the present invention without impairing the fibrinolytic activity of tPA. The peptides of the invention are thus highly useful in treating pathological disorders associated with damage to the central nervous system in situations where tPA is routinely being administered for fibrinolytic therapy as well as in situations where tPA is endogenously secreted.

According to one aspect, the present invention provides an isolated peptide of the amino acid sequence set forth in SEQ ID NO:3:

$R_1$-Arg-Met-Ala-Pro-Glu-Glu-Ile-Ile-Met-Asp-Arg-Pro-Phe-Leu-Phe-Val-Val-Arg-$R_2$ or a fragment thereof, wherein $R_1$ is selected from the group consisting of a hydrogen, acetyl, alkyl, and an amino blocking group; and $R_2$ is selected from the group consisting of a carboxyl, amide, alcohol, ester, and a carboxyl blocking group; and wherein the fragment consists of 7 to 17 amino acid residues comprising the amino acid sequence Glu-Glu-Ile-Ile-Met-Asp as set forth in SEQ ID NO: 11.

According to some embodiments, the peptide has the amino acid sequence selected from the group consisting of:

acetyl-Arg-Met-Ala-Pro-Glu-Glu-Ile-Ile-Met-Asp-Arg-Pro-Phe-Leu-Phe-Val-Val-Arg-amide as set forth in SEQ ID NO: 1;

Arg-Met-Ala-Pro-Glu-Glu-Ile-Ile-Met-Asp-Arg-Pro-Phe-Leu-Phe-Val-Val-Arg as set forth in SEQ ID NO: 4;

acetyl-Arg-Met-Ala-Pro-Glu-Glu-Ile-Ile-Met-Asp-Arg-Pro-Phe-Leu-Phe-Val-Val-Arg as set forth in SEQ ID NO:5; and Arg-Met-Ala-Pro-Glu-Glu-Ile-Ile-Met-Asp-Arg-Pro-Phe-Leu-Phe-Val-Val-Arg-amide as set forth in SEQ ID NO:6.

According to a certain embodiment, the peptide is an 18-mer peptide of the amino acid sequence set forth in SEQ ID NO:1.

According to another aspect, the present invention provides a pharmaceutical composition comprising an isolated peptide of the amino acid sequence set forth in SEQ ID NO:3:

$R_1$-Arg-Met-Ala-Pro-Glu-Glu-Ile-Ile-Met-Asp-Arg-Pro-Phe-Leu-X-Val-Val-Arg-$R_2$ or a fragment thereof, wherein $R_1$ is selected from the group consisting of a hydrogen, acetyl, alkyl, and an amino blocking group; and $R_2$ is selected from the group consisting of a carboxyl, amide, alcohol, ester, and a carboxyl blocking group; and wherein the fragment consists of 7 to 17 amino acid residues comprising the amino acid sequence Glu-Glu-Ile-Ile-Met-Asp of SEQ ID NO: 11, the pharmaceutical composition further comprising a pharmaceutically acceptable carrier.

According to some embodiments, the peptide within the pharmaceutical composition has an amino acid sequence selected from the group consisting of:

acetyl-Arg-Met-Ala-Pro-Glu-Glu-Ile-Ile-Met-Asp-Arg-Pro-Phe-Leu-Phe-Val-Val-Arg-amide as set forth in SEQ ID NO: 1;

Arg-Met-Ala-Pro-Glu-Glu-Ile-Ile-Met-Asp-Arg-Pro-Phe-Leu-Phe-Val-Val-Arg as set forth in SEQ ID NO: 4;

acetyl-Arg-Met-Ala-Pro-Glu-Glu-Ile-Ile-Met-Asp-Arg-Pro-Phe-Leu-Phe-Val-Val-Arg as set forth in SEQ ID NO:5; and Arg-Met-Ala-Pro-Glu-Glu-Ile-Ile-Met-Asp-Arg-Pro-Phe-Leu-Phe-Val-Val-Arg-amide as set forth in SEQ ID NO:6.

According to a certain embodiment, the peptide within the pharmaceutical composition is an 18-mer peptide of the amino acid sequence set forth in SEQ ID NO:1.

According to further aspect, the present invention provides a method for reducing neurological damage in a subject having or at risk of having neurological damage, the method comprising administering to the subject a pharmaceutical composition comprising a therapeutically effective amount of an isolated peptide of the amino acid sequence as set forth in SEQ ID NO7:

$R_1$-Arg-Met-Ala-Pro-Glu-Glu-Ile-Ile-Met-Asp-Arg-Pro-Phe-Leu-$X_1$-Val-Val-Arg-$R_2$ or a fragment thereof, wherein $R_1$ is selected from the group consisting of a hydrogen, acetyl, alkyl, and an amino blocking group; $X_1$ is selected from the group consisting of Tyr and Phe; and $R_2$ is selected from the group consisting of a carboxyl, amide, alcohol, ester, and a carboxyl blocking group; and wherein the fragment consists of 7 to 17 amino acid residues comprising the amino acid sequence Glu-Glu-Ile-Ile-Met-Asp of SEQ ID NO: 11, the pharmaceutical composition further comprising a pharmaceutically acceptable carrier.

According to still further aspect, the present invention provides a method for reducing neurological damage in a subject having or at risk of having neurological damage, the method comprising administering to a subject in need thereof a pharmaceutical composition comprising a therapeutically effective amount of a fibrinolytic agent and an isolated peptide of the amino acid sequence set forth in SEQ ID NO:7:

$R_1$-Arg-Met-Ala-Pro-Glu-Glu-Ile-Ile-Met-Asp-Arg-Pro-Phe-Leu-$X_1$-Val-Val-Arg-$R_2$ or a fragment thereof, wherein $R_1$ is selected from the group consisting of a hydrogen, acetyl, alkyl, and an amino blocking group; $X_1$ is selected from the group consisting of Tyr and Phe; and $R_2$ is selected from the group consisting of a carboxyl, amide, alcohol, ester, and a carboxyl blocking group; and wherein the fragment consists of 7 to 17 amino acid residues comprising the amino acid sequence Glu-Glu-Ile-Ile-Met-Asp of SEQ ID NO: 11, the pharmaceutical composition further comprising a pharmaceutically acceptable carrier.

According to some embodiments, the peptide to be used for reducing the neurological damage has an amino acid sequence selected from the group consisting of SEQ ID NOs: 1, 2, 4-6, 8-10. According to a certain embodiment, the peptide to be used has the amino acid sequence as set forth in SEQ ID NO:1. According to another embodiment, the peptide to be used has the amino acid sequence as set forth in SEQ ID NO:2.

According to additional embodiments, the neurological damage is attributed to a stroke, brain injury including, but not limited to, traumatic brain injury (TBI) and ischemic brain injury, spinal cord injury, brain surgery, cardiac surgery, and neurological disease.

According to further embodiments, the neurological disease is selected from the group consisting of Alzheimer's disease, Huntington's disease, Parkinson's disease, and amyotrophic lateral disease.

According to yet further embodiments, the pharmaceutical composition is administered by intravenous, subcutaneous, intramuscular, intraperitoneal, oral, topical, intradermal, transdermal, intranasal, epidural, ophthalmic, vaginal or rectal administration route. According to a certain embodiment, the pharmaceutical composition is administered by intravenous injection and/or infusion.

According to some embodiments, the fibrinolytic agent is selected from the group consisting of tPA, uPA, scuPA, tcuPA, streptokinase, rt-PA, alteplase, reteplase, lanoteplase, TNK-rt-PA, anisoylated plasminogen streptokinase complex, anistreplase, and derivatives thereof.

According to additional embodiments, the 18-mer peptide or fragment thereof is administered after administration of the fibrinolytic agent.

According to further aspect, the present invention provides a method for fibrinolytic therapy comprising administering to a subject in need thereof a pharmaceutical composition comprising a therapeutically effective amount of a fibrinolytic agent and an isolated peptide of the amino acid sequence set forth in SEQ ID NO:7:

$R_1$-Arg-Met-Ala-Pro-Glu-Glu-Ile-Ile-Met-Asp-Arg-Pro-Phe-Leu-$X_1$-Val-Val-Arg-$R_2$ or a fragment thereof, wherein $R_1$ is selected from the group consisting of a hydrogen, acetyl, alkyl, and an amino blocking group; $X_1$ is selected from the group consisting of Tyr and Phe; and $R_2$ is selected from the group consisting of a carboxyl, amide, alcohol, ester, and a carboxyl blocking group, with the proviso that the peptide set forth in SEQ ID NO: 2 is excluded; and wherein the fragment consists of 7 to 17 amino acid residues comprising the amino acid sequence Glu-Glu-Ile-Ile-Met-Asp of SEQ ID NO: 11, the pharmaceutical composition further comprising a pharmaceutically acceptable carrier.

According to some embodiments, the peptide to be used for the fibrinolytic therapy has an amino acid sequence selected from the group consisting of SEQ ID NOs:1, 4-6, 8-10. According to a certain embodiment, the peptide to be used has the amino acid sequence as set forth in SEQ ID NO:1.

According to additional embodiments, the fibrinolytic agent is selected from the group consisting of tPA, uPA, scuPA, tcuPA, streptokinase, rt-PA, alteplase, reteplase, lanoteplase, TNK-rt-PA, anisoylated plasminogen streptokinase complex, anistreplase, and derivatives thereof.

According to further embodiments, the pharmaceutical composition is administered by intravenous, subcutaneous, intramuscular, intraperitoneal, oral, topical, intradermal, transdermal, intranasal, epidural, ophthalmic, vaginal or rectal administration route. According to a certain embodiment, the pharmaceutical composition is administered by intravenous injection and/or infusion.

According to yet further embodiments, the peptide or fragment thereof is administered after administration of the fibrinolytic agent.

According to yet further aspect, the present invention provides use of an isolated peptide of the amino acid sequence set forth in SEQ ID NO:7:

$R_1$-Arg-Met-Ala-Pro-Glu-Glu-Ile-Ile-Met-Asp-Arg-Pro-Phe-Leu-$X_1$-Val-Val-Arg-$R_2$ or a fragment thereof, wherein $R_1$ is selected from the group consisting of a hydrogen, acetyl, alkyl, and an amino blocking group; $X_1$ is selected from the group consisting of Tyr and Phe; and $R_2$ is selected from the group consisting of a carboxyl, amide, alcohol, ester, and a carboxyl blocking group; and wherein the fragment consists of 7 to 17 amino acid residues comprising the amino acid sequence Glu-Glu-Ile-Ile-Met-Asp of SEQ ID NO: 11, for reducing neurological damage according to the principles of the present invention.

According to another aspect, the present invention provides use of a fibrinolytic agent and an isolated peptide of the amino acid sequence set forth in SEQ ID NO:7:

$R_1$-Arg-Met-Ala-Pro-Glu-Glu-Ile-Ile-Met-Asp-Arg-Pro-Phe-Leu-$X_1$-Val-Val-Arg-$R_2$ or a fragment thereof, wherein $R_1$ is selected from the group consisting of a hydrogen, acetyl, alkyl, and an amino blocking group; $X_1$ is selected from the group consisting of Tyr and Phe; and $R_2$ is selected from the group consisting of a carboxyl, amide, alcohol, ester, and a carboxyl blocking group; and wherein the fragment consists of 7 to 17 amino acid residues comprising the amino acid sequence Glu-Glu-Ile-Ile-Met-Asp of SEQ ID NO: 11, for reducing neurological damage according to the principles of the present invention.

According to yet further aspect, the present invention provides use of a fibrinolytic agent and an isolated peptide of the amino acid sequence set forth in SEQ ID NO:7:

$R_1$-Arg-Met-Ala-Pro-Glu-Glu-Ile-Ile-Met-Asp-Arg-Pro-Phe-Leu-$X_1$-Val-Val-Arg-$R_2$ or a fragment thereof, wherein $R_1$ is selected from the group consisting of a hydrogen, acetyl, alkyl, and an amino blocking group; $X_1$ is selected from the group consisting of Tyr and Phe; and $R_2$ is selected from the group consisting of a carboxyl, amide, alcohol, ester, and a carboxyl blocking group, with the proviso that the peptide set forth in SEQ ID NO: 2 is excluded; and wherein the fragment consists of 7 to 17 amino acid residues comprising the amino acid sequence Glu-Glu-Ile-Ile-Met-Asp of SEQ ID NO: 11, for fibrinolytic therapy.

These and further embodiments will be apparent from the figures, detailed description and examples that follow.

DETAILED DESCRIPTION OF THE INVENTION

Figure 1:
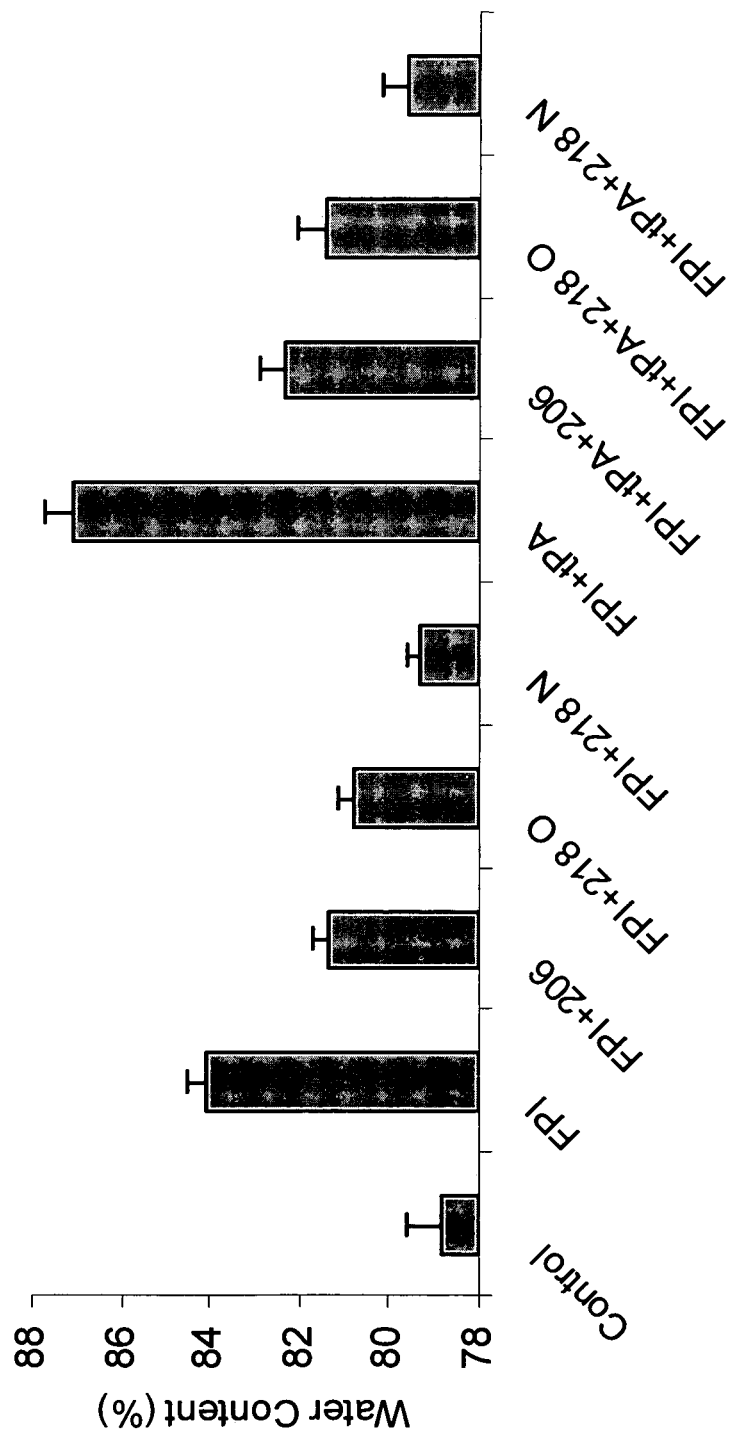
FIG. 1 demonstrates the effect of peptide 218 O (an 18-mer peptide analog of the sequence Ac-RMAPEEIIMDRPFLY-VVR-amide as set forth in SEQ ID NO: 2), peptide 218 N (an 18-mer peptide corresponding to amino acid residues 369-386 of human PAI-1 having the sequence Ac-RMAPEEIIM-DRPFLFVVR-amide as set forth in SEQ ID NO: 1), and peptide 206 (a 6-mer peptide of the sequence EEIIMD as set forth in SEQ ID NO: 11 corresponding to amino acid residues 373-378 of human PAI-1) on post-traumatic brain injury (TBI) brain water content in pigs. The animals were exposed to fluid percussion brain injury (FPI), FPI+peptide 206, peptide 218 O, or Peptide 218 N (1 mg/kg i.v.), FPI+tPA (2 mg/kg i.v.), FPI+tPA+peptide 206, FPI+tPA+peptide 218 O, or FPI+tPA+peptide 218 N. Results (mean±SE) from 7 animals in each group are shown.

The present invention is based in part on the findings that 18-mer peptides corresponding to amino acids 369-386 of human PAI-1 were capable of decreasing the tPA-induced increase in brain infarct volume or in water content in mechanical models of stroke in rats and pigs. The present findings have also indicated that the peptides were capable of reducing brain edema after traumatic brain injury in pigs that were not subjected to any treatment with exogenous tPA. Thus, the peptides of the present invention were effective in eliminating the deleterious side effects induced by endogenous and/or exogenous tPA without abolishing its beneficial fibrinolytic activity.

The neuroprotective activity exerted by the peptides of the present invention is higher than that obtained by a 6-mer peptide having the amino acid sequence EEIIMD of SEQ ID NO: 11. Without wishing to be bound by any mechanism of action, it is suggested that the segment EEIIMD of SEQ ID NO: 11 is responsible for some neuroprotective activity, however, the contribution of the adjacent amino acid residues to peptide stability and/or peptide conformation is highly important as it significantly improves the neuroprotective activity exerted by the 6-mer peptide.

The present invention provides an isolated 18-mer peptide having the amino acid sequence $R_1$-RMAPEEIIMDRP-FLFVVR—$R_2$ as set forth in SEQ ID NO:3, or a fragment thereof, wherein the fragment consists of 7 to 17 amino acid residues comprising the sequence EEIIMD.

Specifically, the present invention relates to the following peptides:

```
1) Ac-RMAPEEIIMDRPFLFVVR-amide    (SEQ ID NO: 1)
designated herein below 218 N*

2) Ac-RMAPEEIIMDRPFLYVVR-amide    (SEQ ID NO: 2)
designated herein below 218 O**

3) RMAPEEIIMDRPFLFVVR             (SEQ ID NO: 4)

4) Ac-RMAPEEIIMDRPFLFVVR          (SEQ ID NO: 5)

5) RMAPEEIIMDRPFLFVVR-amide       (SEQ ID NO: 6)

6) RMAPEEIIMDRPFLYVVR             (SEQ ID NO: 8)

7) Ac-RMAPEEIIMDRPFLYVVR          (SEQ ID NO: 9)

8) RMAPEEIIMDRPFLYVVR-amide       (SEQ ID NO: 10)

9) EEIIMD                         (SEQ ID NO: 11)
designated herein below 206

10) Full-length amino acid        (SEQ ID NO: 12)
sequence of human PAI-1
*N refers to new;
**O refers to old.
```

$R_1$-Arg-Met-Ala-Pro-$X_1$-$X_2$-Ile-Ile-Met-$X_3$-Arg-Pro-Phe-Leu-$X_4$-Val-Val-Arg-$R_2$

The present invention provides 7 to 18-mer peptides comprising the amino acid sequence EEIIMD. However, it is to be understood that within the scope of the present invention is included a peptide having the amino acid sequence of general formula I:

$R_1$-Arg-Met-Ala-Pro-$X_1$-$X_2$-Ile-Ile-Met-$X_3$-Arg-Pro-Phe-Leu-$X_4$-Val-Val-Arg-$R_2$ or a fragment thereof, wherein $R_1$ is selected from the group consisting of a hydrogen, acetyl, alkyl, and an amino blocking group; $X_1$ is selected from the group consisting of Asp, Glu, and Arg; $X_2$ is selected from the group consisting of Asp and Glu; $X_3$ is selected from the group consisting of Asp and Glu; $X_4$ is selected from the group consisting of Phe and Tyr; and $R_2$ is selected from the group consisting of a carboxyl, amide, alcohol, ester, and a carboxyl blocking group; and wherein the fragment consists of 7 to 17 amino acid residues comprising the amino acid sequence $X_1$-$X_2$-Ile-Ile-Met-$X_3$, with the proviso that the peptide having the amino acid sequence acetyl-RMAPEEIIMDRPFLYVVR-amide set forth in SEQ ID NO:2 is excluded.

Thus, the present invention provides 7 to 18-mer peptides comprising the sequence EEIIMD of SEQ ID NO: 11 and analogs thereof. Uses of the peptides, including the peptide of SEQ ID NO: 2, for reducing neurological damage are encompassed in the present invention. Also included are uses of these peptides, excluding the peptide of SEQ ID NO: 2, in fibrinolytic therapy.

The term "peptide" as used throughout the specification and claims designates a linear series of amino acid residues connected one to the other by peptide bonds. The amino acid residues are represented throughout the specification and claims by one-letter or three-letter codes according to IUPAC conventions.

The term "amino acid" or "amino acid residue" is understood to include the 20 naturally occurring amino acids.

The peptides of the present invention consist of 7 to 18 amino acid residues.

The peptides of the present invention can be isolated by any protein purification method known in the art. For example, PAI-1 can be subjected to one or more proteolytic enzymes to yield, a mixture of peptides, which can further be purified by any protein purification method known in the art to obtain the isolated peptides. Alternatively or additionally, PAI-1 can be cleaved by chemical agents such as, for example, CNBr to yield a mixture of peptides that can be further purified to obtain isolated peptides.

The peptides of the present invention can also be prepared by methods well known in the art including chemical synthesis or recombinant DNA technology.

A preferred method of synthesizing the peptides of the present invention involves solid-phase peptide synthesis utilizing a solid support as described by Merrifield (see J. Am. Chem. Soc., 85:2149, 1964). Large-scale peptide synthesis is described, for example, by Andersson et al. (Biopolymers 55(3): 227-50, 2000). Examples of solid phase peptide synthesis methods include the BOC method, which utilizes tert-butyloxcarbonyl as the α-amino protecting group, and the FMOC method, which utilizes 9-fluorenylmethyloxcarbonyl to protect the α-amino of the amino acid residues, both methods are well-known by those of skill in the art. Alternatively, the peptides of the present invention can be synthesized by standard solution synthesis methods (see, for example, Bodanszky, M., Principles of Peptide Synthesis, Springer-Verlag, 1984).

The peptides according to the principles of the invention need not consist of an amino acid sequence identical to RMAPEEIIMDRPFLFVVR set forth in SEQ ID NO:4 or RMAPEEIIMDRPFLYVVR set forth in SEQ ID NO:8 so long as each of the peptide analogs is capable of reducing, preventing and/or inhibiting neurological damage.

The term "analog" includes any peptide comprising altered sequence by amino acid substitutions, deletions, or chemical modifications of the peptides listed herein above and which displays neuroprotective activity. By using "amino acid substitutions", it is meant that functionally equivalent amino acid residues are substituted for residues within the sequence resulting in a silent change. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are known as conservative substitutions. Additionally, a non-conservative substitution may be made so long as the neuroprotective activity of the peptide is maintained. It will be appreciated that the present invention encompasses peptide analogs, wherein at least one amino acid is substituted by another amino acid to produce a peptide analog having increased stability or longer half-life as compared to the peptides listed herein above.

While the amino acid residues of the peptide sequences set forth herein above are all in the "L" isomeric form, residues in the "D" isomeric form can substitute any L-amino acid residue so long as the peptide analog retains neuroprotective activity. Production of a retro-inverso D-amino acid peptide analog where the peptide is made with the same amino acids as disclosed, but at least one amino acid, and perhaps all amino acids are D-amino acids is well known in the art. When all of the amino acids in the peptide analog are D-amino acids, and the N- and C-terminals of the peptide analog are reversed, the result is an analog having the same structural groups being at the same positions as in the L-amino acid form of the peptide. However, the peptide analog is more stable to proteolytic degradation and is therefore useful in many of the applications recited herein.

The present invention further encompasses peptide derivatives of the peptides listed herein above. The term "derivative" refers to a peptide having an amino acid sequence that comprises the amino acid sequence of the peptide of the invention, in which one or more of the amino acid residues is subjected to chemical derivatizations by a reaction of side chains or functional groups, where such derivatizations do not destroy the neuroprotective activity of the peptide derivative. Chemical derivatization of amino acid residues include, but are not limited to, acetylation, amidation, glycosylation, oxidation, reduction, myristylation, sulfation, acylation, ADP-ribosylation, cyclization, disulfide bond formation, hydroxylation, iodination, and methylation.

The peptide derivatives according to the principles of the present invention also include bond modifications, including but not limited to $CH_2$—NH, $CH_2$—S, $CH_2$—S=O, O=C—NH, $CH_2$—O, $CH_2$—$CH_2$, S=C—NH, CH=CH, and CF=CH and backbone modifications. Peptide bonds (—CO—NH—) within the peptide may be substituted, for example, by N-methylated bonds (—N($CH_3$)—CO—); ester bonds (—C(R)H—C—O—O—C(R)—N); ketomethylene bonds (—CO—CH2-); α-aza bonds (—NH—N(R)—CO—), wherein R is any alkyl group, e.g., methyl; carba bonds (—$CH_2$—NH—); hydroxyethylene bonds (—CH(OH)—CH2-); thioamide bonds (—CS—NH—); olefinic double bonds (—CH=CH—); and peptide derivatives (—N(R)—$CH_2$—CO—), wherein R is the "normal" side chain, naturally presented on the carbon atom. These modifications can occur at any of the bonds along the peptide chain and even at several (2-3) at the same time.

Blocking groups are well known to those of skill in the art as are methods of coupling such groups to the appropriate residue(s) comprising the peptides of the present invention (see, e.g., Greene et al., (1991) Protective Groups in Organic Synthesis, 2nd ed., John Wiley & Sons, Inc. Somerset, N.J.).

In certain embodiments, the terminal amino acids of the peptides of the invention are blocked with a protecting or blocking group. A wide number of blocking groups are suitable for this purpose. Such groups include, but are not limited to, acetyl, amide, and alkyl groups with acetyl and alkyl groups being particularly preferred for N-terminal protection and amide groups being preferred for carboxyl terminal protection. In certain embodiments, an acetyl group is used to protect the amino terminus and an amide group is used to protect the carboxyl terminus. In certain embodiments, the protecting groups can include alkyl chains as in fatty acids, propeonyl, formyl, and others. Particularly preferred carboxyl blocking groups include amides, esters, and ether-forming blocking groups. Other blocking groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethylbenzene-sulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylid-ene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA).

Also included as chemical derivatives are those peptides which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine. The peptides may also contain non-natural amino acids. Examples of non-natural amino acids are norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala). The peptides may also contain non-protein side chains. In addition to the above, the peptides of the present invention may also include one or more non-amino acid monomers (e.g., fatty acids, complex carbohydrates, and the like).

The present invention includes conjugates of the peptides of the invention. The term "conjugate" is meant to define a peptide of the present invention coupled to or conjugated with another protein or polypeptide. Such conjugates may have advantages over the peptides themselves. Such conjugates can be made by protein synthesis, e.g., by use of a peptide synthesizer, or by ligating the appropriate nucleic acid sequences encoding the desired amino acid sequences to each other by methods known in the art, in the proper coding frame, and expressing the chimeric protein by methods commonly known in the art.

A peptide of the present invention may also be conjugated to itself or aggregated in such a way as to produce a large complex containing the peptide. Such large complexes may be advantageous because they may have new biological properties such as longer half-life in circulation or greater activity.

Pharmaceutical Compositions and Administration Routes

The present invention provides methods for preventing neurological damage or the progression of neurological damage in a subject suffering from or susceptible to such neurological damage comprising administering to the subject a pharmaceutical composition comprising a therapeutically effective amount of a peptide of the invention and a pharmaceutically acceptable carrier.

As used herein, the term "pharmaceutical composition" refers to a preparation of one or more of the peptides described herein with other chemical components such as pharmaceutically acceptable carriers and excipients. The purpose of a pharmaceutical composition is to facilitate administration of an active ingredient to an organism.

The term "pharmaceutically acceptable" means approved by a regulatory agency of the Federal or a state government or listed in the U.S. Pharmacopeia or other generally recognized pharmacopeia for use in animals, and more particularly in humans.

The pharmaceutical compositions of the present invention can be formulated as pharmaceutically acceptable salts of the peptides of the present invention. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the peptide of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

The term "carrier" refers to a diluent or vehicle that does not cause significant irritation to an organism and does not abrogate the biological activity and properties of the administered compound. An adjuvant is included under these phrases. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions.

The pharmaceutical compositions of the invention can further comprise an excipient. Herein, the term "excipient" refers to an inert substance added to a pharmaceutical composition to further facilitate administration of an active ingredient. Suitable pharmaceutical excipients include starch, glucose, lactose, sucrose, trehalose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned.

The pharmaceutical compositions of the present invention can be manufactured by processes well known in the art, e.g., by means of conventional mixing, dissolving, granulating, dragee-making, levigating, emulsifying, encapsulating, entrapping, or lyophilizing processes.

Typically, pharmaceutical compositions, which contain peptides as active ingredients are prepared as injectable, either as liquid solutions or suspensions, however, solid forms, which can be suspended or solubilized prior to injection, can also be prepared. The compositions can also take the form of emulsions, tablets, capsules, gels, syrups, slurries, powders, creams, depots, sustained-release formulations and the like.

Methods of introduction of a pharmaceutical composition comprising a peptide of the invention include, but are not limited to, intravenous, subcutaneous, intramuscular, intraperitoneal, oral, topical, intradermal, transdermal, intranasal, epidural, ophthalmic, vaginal and rectal routes. The pharmaceutical compositions can be administered by any convenient route, for example by infusion or bolus injection, by absorption through epithelial linings (e.g., oral mucosa, rectal and intestinal mucosa, etc.), and may be administered together with other therapeutically active agents. The administration may be localized, or may be systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or neubilizer.

Pharmaceutical compositions for use in accordance with the present invention may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal or transdermal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a neubilizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, traditional binders and carriers such as triglycerides, microcrystalline cellulose, gum tragacanth or gelatin.

It may be desirable to administer the pharmaceutical composition of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material. Administration can also be by direct injection e.g., via a syringe, at the site of injury.

For directed internal topical applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to materials of the above type, a liquid carrier such as fatty oil. In addition, dosage unit forms can contain other materials which modify the physical form of the dosage unit, for example, coatings of sugar, shellac, or other enteric agents.

A peptide of the invention can be delivered in a controlled release system. For example, the peptide can be administered in combination with a biodegradable, biocompatible polymeric implant, which releases the peptide over a controlled period of time at a selected site. Examples of, preferred polymeric materials include polyanhydrides, polyorthoesters, polyglycolic acid, polylactic acid, polyethylene vinyl acetate, copolymers and blends thereof. (See, Medical applications of controlled release, Langer and Wise (eds.), 1974, CRC Pres., Boca Raton, Fla.). A controlled release system can be placed in proximity of the therapeutic target, thus requiring only a fraction of a systemic dose.

Pharmaceutical compositions suitable for use in the context of the present invention include compositions wherein the peptides are contained in an amount effective to achieve the intended purpose. More specifically, a "therapeutically effective amount" means an amount of a peptide effective to prevent, alleviate, or ameliorate symptoms of a condition or disease associated with neurological damage in the subject being treated.

Uses of the Peptides

The present invention provides uses of the peptides of the invention for the treatment, prophylaxis and/or inhibition of neurological damage in a subject in need thereof, for the treatment of hypoxic or ischemic stroke, for the treatment of brain injury, and/or for the treatment of neurological diseases.

It will be appreciated that the term 'treatment' as used herein includes both treatment and/or prophylactic use of the pharmaceutical compositions comprising the peptides of the invention. In the present invention prophylactic use of the pharmaceutical compositions comprises administering to a subject in need thereof the pharmaceutical composition to prevent the onset of neurological damage; and to prevent the progression of neurological damage.

The peptides of the present invention have neuroprotective activity. The term "neuroprotective activity" refers to prevention of onset of neurological damage or arresting or inhibition of progression of neurological damage in a subject.

The term "neurological damage" as used throughout the specification and claims includes, but is not limited to, brain infarct, brain edema, hemorrhage, and neurodegeneration.

The treatment of the present invention can be applied to a variety of acute and chronic conditions which lead to neurological damage.

Thus, the present invention can be used for the treatment of ischemic conditions, for example cerebral ischemia (thromboembolic or hypoxic or ischemic stroke, hemorrhage or brain injury as a result of trauma) which involve various forms of brain damage and may lead to acute or delayed damage to the brain neurons, and to neurodegeneration—for example after head trauma.

The present invention can be applicable to the treatment of relatively long-term neurodegeneration of non-ischemic origin (e.g., epilepsy, Alzheimer's disease, Huntington's disease, Downs syndrome, Multiple Sclerosis and Parkinson's disease) and neurological damage resulting from chronic infection, for example HIV producing the syndrome of AIDS.

Other conditions which can cause neurological damage are well-known to an ordinarily skilled neurologist or similar physician and include: primary neurodegenerative disease; spinal cord lesions; hypoxic processes such as perinatal hypoxia or ischemic processes such as subsequent to cardiac arrest; neurotrauma such as subsequent to cardiac bypass surgery or grafting; metabolically induced neurological damage; cerebral seizures; secondary neurodegenerative diseases (metabolic or toxic); memory disorders; vascular dementia, multi-infarct dementia, Lewy body dementia, or neurogenerative dementia.

The time of treatment is also significant and can be important. Administration can be before or after neurological damage has occurred or is suspected. Administration before neurological damage has occurred can be of value for prophylactic treatment, for example when the subject is considered to be at risk of an ischemic condition. Such conditions could be, for example in cardiac bypass surgery, in which a significant proportion of patients can suffer minor cerebral damage, or in childbirth, in which the fetus may be liable to problems in the fetal circulation potentially leading to anoxia and cerebral palsy and the like. The more common time of administration is after neurological damage has occurred or is suspected, for example in the conditions of treating a stroke or a head injury, and in such cases it is desirable to make the administration as soon as possible after the event to get best results—preferably within an hour or less, though administration later than that time can still be beneficial.

According to some embodiments, the subject is a mammal. According to a certain embodiment, the mammal is a human.

Determination of a therapeutically effective amount is well within the capability of those skilled in the art, especially in light of the detailed, disclosure provided herein.

The precise amount of the peptide administered to a particular subject, preferably a mammal, more preferably a human being, in the method of treatment of the present invention will depend on a number of factors, for example the specific peptide administered; its mode of administration and/or the use for which it is intended; the particular clinical condition being treated and/or its severity; and/or the age, body mass and/or past clinical history of the patient to be treated, and always lies within the sound discretion of the person administering and/or supervising the treatment, for example a medical practitioner such as nurse and/or physician. Nevertheless, a suitable daily dose of the peptide for administration to a mammal is generally from about 0.01 mg/day per kg of the mammal's body mass to about 80 mg/kg/day, more usually 0.2-40 mg/kg/day given in a single dose and/or in divided doses at one or more times during the day. The pharmaceutical composition can contain from about 0.1% to about 99% by weight of the peptide and is generally prepared in unit dose form, a unit dose of a peptide generally being from about 0.1 mg to about 500 mg.

Dosage amount and administration intervals may be adjusted individually to provide sufficient plasma or local levels of the peptide to induce a neuroprotective effect.

Depending, on the severity and responsiveness of the condition to be treated, dosing can be of a single or a plurality of administrations, with course of treatment lasting from several days to several weeks, or until cure is effected or diminution of the disease state is achieved.

The following examples are intended to be merely illustrative in nature and to be construed in a non-limitative fashion.

EXAMPLES

The examples herein below describe the effect of a PAI-1 derived 18-mer peptide acetyl-RMAPEEIIMDRPFLFVVR-amide of SEQ ID NO: 1 on neurotoxicity induced by exogenous tPA during treatment of stroke, and on endogenous tPA released after brain trauma.

Materials

Recombinant tPA was purchased from Genentech, Inc., South San Francisco, Calif. Peptides 206, 218 O, and 218 N were synthesized by Peptisyntha SA, Bruxelles-Belgique.

Methods

Fluid Percussion Brain Injury (FPI) method. The method was performed as described by Armstead et al., Nat. Neurosci. 9: 1150-1155 (2006).

MCA occlusion. All studies were conducted in accordance with the NIH Guide for the Care and Use of Laboratory Animals. Sprague-Dawley rats (mean weight 250 g) were fed on regular chow and allowed free access to drinking water. Rats were anesthetized with an i.p. injection of ketamine (75 mg per ml, Apharmo) and xylazine (5 mg per ml, Bayer). Body temperature was maintained at $37\pm0.5°$ C. by means of a heating lamp. Focal cerebral ischemia was induced by occluding the left MCA with an intraluminal filament (Ding-Zhou, L. et al. 2002 Eur J. Pharmacol. 457, 137-146). Briefly, the left common and external carotid arteries were isolated through a midline neck incision and ligated with a 4-0 silk suture (Ethicon). An arteriotomy was fashioned in the common carotid artery just proximal to the carotid bifurcation. A 4-0 nylon monofilament (Ethicon) was introduced through this incision into the internal carotid artery and advanced distal to the carotid bifurcation to occlude the origin of the MCA; the thread was carefully withdrawn 2 hours later. tPA alone at the indicated concentrations, tPA together with the PAI-1 derived peptides 206 (EEIIMD of SEQ ID NO: 11) or peptide 218 N (Ac-RMAPEEIIMDRPFLFVVR-amide of SEQ ID NO: 1) or peptide 218 O (Ac-RMAPEEIIMDRPFLYVVR-amide of SEQ ID NO: 2) were injected i.v. 2 hours after the thread had been withdrawn. Rats were returned to their cages after recovering from anesthesia. Twenty-four hours later. rats were euthanized with an overdose of Nembutal and the infarct size was measured.

Embolic stroke Embolic stroke was induced according to the previously reported microembolism model (Bdeir, K. et al. 2000 Blood 96, 1820-1826) as adapted to stroke (Atochin, D. N. et al. 2004. Stroke 35, 2177-2182). Microemboli were prepared, dissected, and homogenized as described (Bdeir K et al. 2000, supra). The suspension of microemboli used to induce stroke contained $1.4\times10^6$ microparticles, with an average diameter of 3 μm.

Experiments were performed in rats as described previously (Ding-Zhou, L. et al. 2002, supra) with some modifications. Briefly, Sprague-Dawley rats (mean weight 250 g) were anesthetized by i.p. injection of ketamine (75 mg per mL) and xylazine (5 mg per mL). The carotid artery was exposed and an arteriotomy was performed. A polyethylene catheter with an inner diameter of 0.02 mm was used to inject the solution of microemboli ($1.4 \times 10^6$ particles) directly into the exposed internal carotid artery. The catheter was flushed with 0.25 ml normal saline and carefully withdrawn. After washing the surgical site with saline containing 1 mM hexacapron, the incision was closed.

After induction of embolic stroke, rats were divided into 4 treatment groups (n=7 each): tPA (6 mg per kg) or tPA (6 mg per kg) with either peptide 206, peptide 218 O, or peptide 218 N (1 mg per kg) in normal saline were injected i.v., 2 hours after the catheter was withdrawn. Control groups received a vehicle consisting of normal saline alone or peptides 206 or 218 (1 mg per kg) in saline. 50% of the dose was given as a bolus injection and the remainder was infused over 60 min. The rats were returned to their cages after recovering from anesthesia. Twenty-four hours after the procedure, the rats were euthanized with an overdose of Nembutal and the infarct size was measured.

Measuring infarct volume The brain was removed and sectioned coronally into 2-mm segments. Brain slices were immersed in 2% 2,3,5-triphenyltetrazolium chloride (TTC) in saline, incubated for 30 minutes at 37° C. and placed in 4% formalin/PBS overnight. The area of infarction remains unstained, appearing white, making it clearly distinguishable from stained viable tissue. The sections were photographed and the infarct area measured using the NIH computer image analysis program. Infarct volume was defined as the sum of the unstained areas of all sections, multiplied by their thickness and expressed in cubic millimeters. Data are represented as mean±SE. Differences were analyzed by ANOVA followed by the t-test and the level of significance was corrected using a post-hoc analysis with the Bonferroni test. Statistical significance was set at $P<0.05$.

Brain water content Brain water content (BWC) was determined by measuring the wet and dry weights of the brain tissue and by using the formula BWC=wet weight-dry weight/wet weight×100. Data were analyzed by analysis of variants with a Student-Newman-Keuls post-hoc test. A $P<0.05$ was considered significant.

Statistical analysis: Where indicated, differences were analyzed by ANOVA followed by the t-test. Analysis of variance was determined in piglet FPI studies with the Student-Newman-Keuls test. The level of significance was corrected using a post-hoc analysis with Bonferroni test. Statistical significance was set at $P<0.05$ and values are presented as mean±SEM.

Example 1

Effect of tPA and PAI-1 Derived Peptides on Brain Water Content after Fluid Percussion Brain Injury (FPI)

Endogenous tPA has been shown to be deleterious in models of brain trauma and to increase post trauma brain edema. To examine the effect of the PAI-1 derived peptides on endogenous tPA-induced increase in brain water content, piglets were given peptide 206, peptide 218 O, peptide 218 N (1 mg/kg, i.v.), or vehicle (0.9% saline) as a control 30 min prior to FPI (injury level 1.9±0.1 atm). In other set of experiments piglets were given tPA alone (2 mg/kg, i.v.), tPA with peptide 206, tPA with peptide 218 O, or tPA with peptide 218 N (1 mg/kg, i.v.) as is shown in FIG. 1.

Brain water content (BWC) was determined by measuring the wet and dry weights of the brain tissue and by using the formula BWC=wet weight-dry weight/wet weight×100. Data were analyzed by analysis of variants with a Fischer's post-hoc test. A $P<0.05$ was considered significant.

Posttraumatic brain edema was assessed by measuring brain water content. Normal water content (78.87±0.75%) was increased (to 84.1±0.45%) after injury in vehicle-treated animals ($P<0.05$). This posttraumatic increase in brain water content was largely inhibited by peptide 206 (81.379±0.3%; $P<0.05$; FIG. 1). FIG. 1 also shows that the 18-mer peptide analog designated 218 O was as effective as peptide 206, while the 18-mer native peptide designated 218 N was significantly more effective than peptide 206 or peptide 218 O in inhibiting the posttraumatic brain edema by decreasing post TBI BWC to 79.343±0.25 ($P<0.05$).

Furthermore, peptide 218 N was significantly more effective than peptide 206 or peptide 218 O in inhibiting the exacerbated increase in brain water content induced by FPI in the presence of tPA. Peptide 218 N decreased the brain water content from 87.12±0.6 to 79.643±0.51, while reduction by peptide 206 was only to 82.351±0.55 ($P<0.05$; FIG. 1).

Example 2

Figure 2:
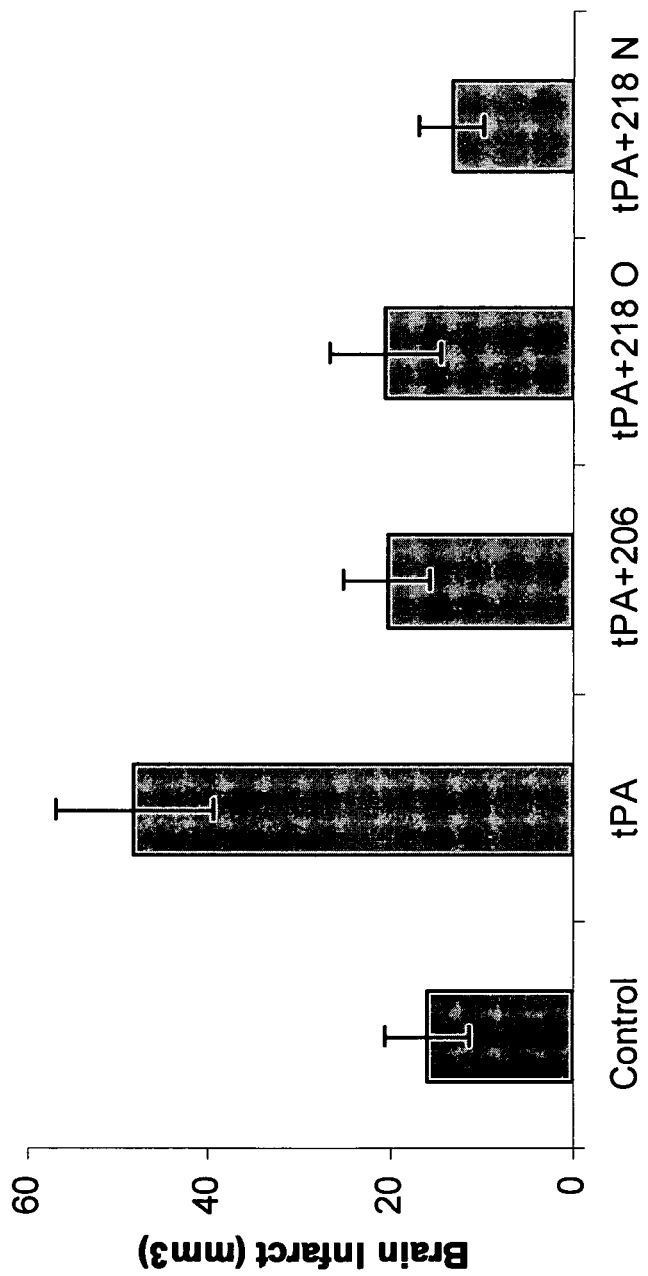
FIG. 2 shows a comparison of the neuroprotective effect of the PAI-1 derived peptides: 206, 218 O, and 218 N, in rats treated with tPA after mechanical obstruction of the MCA. Control rats received saline. The results shown are the mean±SE of infarct size in 10 rats in each group.

Effects of tPA and PAI-1 Derived Peptides in Rats after Mechanical Obstruction and Embolic Stroke The effect of the PAI-1 derived peptides on infarct size after transient mechanical obstruction of the MCA in rats treated with tPA was examined. tPA injected intravenously two hours after establishing reperfusion increased the infarct size from 16±4.6 to 48.333±8.7 mm3 (FIG. 2). Co-injection of peptide 206, peptide 218 O, or peptide 218 N significantly reduced the infarct size associated with the tPA treatment (FIG. 2) ($P<0.01$). Moreover, FIG. 2 shows that peptide 218 N was more effective than peptide 206 or peptide 218 O in preventing the tPA induced infarct size enlargement. The infarct size measured in the presence of peptide 206 was 20.333±4.8 while in the presence of peptide 218 N its size was only 13.3±3.6 mm3 ($P<0.05$; FIG. 2).

Figure 3:
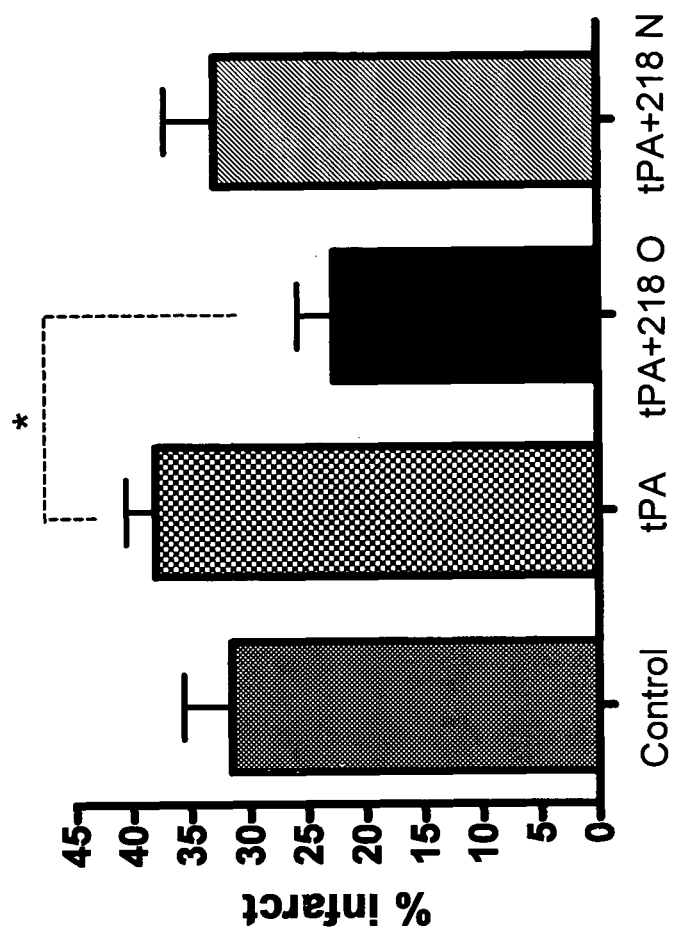
FIG. 3 shows a comparison of the neuroprotective effect of the PAI-1 derived peptides: 206, 218 O, and 218 N, in rats treated with tPA after mechanical obstruction of the MCA. Control rats received saline.

A similar experiment in which 50% of the tPA dose was given by bolus injection and the remainder was infused during 60 min showed that peptide 218 O was more effective than peptide 218 N in reducing infarct volume (FIG. 3)

Figure 4:
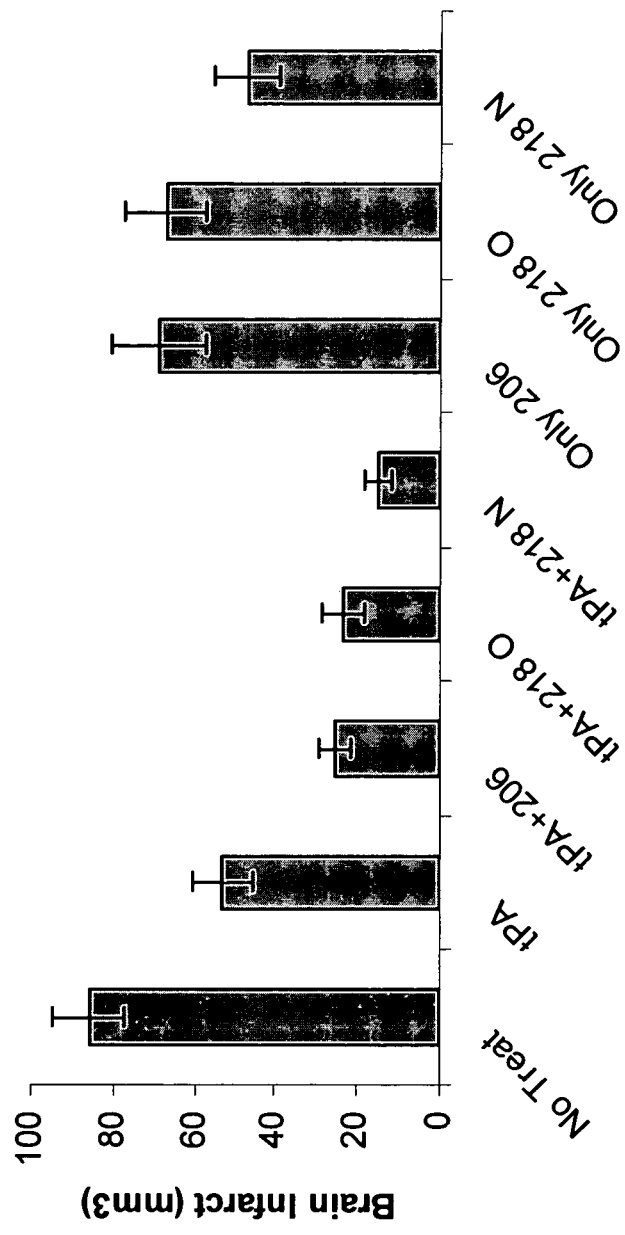
FIG. 4 shows a comparison of the neuroprotective effect of the PAI-1 derived peptides: 206, 218 O, and 218 N, in rats treated with tPA after embolic stroke. Control rats received saline. The results shown are the mean±SD of the infarct size in 10 rats per group.

The effect of PAI-1 derived peptides on tPA treated rats after embolic stroke induced by injection of microthrombi directly into the MCA was also examined. Two hours after embolization, rats were treated i.v. with either tPA alone, tPA with peptide 206, tPA with peptide 218 O, tPA with peptide 218 N, normal saline or peptides 206, 218 O, 218 N alone. Injection of tPA decreased infarct volume by approximately 48% (FIG. 4), which contrasts with its deleterious effect after mechanical stroke (FIGS. 2 and 3). However, animals treated with tPA and PAI-1 derived peptides had significantly ($P<0.01$) smaller infarct volumes than those treated with tPA alone (FIG. 4). Furthermore, animals treated with tPA and peptide 218 N had smaller infarct volumes than those treated with tPA and peptide 206 or tPA and peptide 218 O ($P<0.05$) (FIG. 4).

As is also shown in FIG. 4, peptide 218 N administered alone significantly reduced post-stroke infarct size ($P<0.05$). This is in contrast to peptides 206 or 218 O that by themselves have little effect on infarct size in the absence of tPA.

Example 3

Effect of PAI-1 Derived Peptides on the Opening of the BBB by tPA

C57/B16 mice received intravenously saline, saline containing 10 mg/kg tPA with or without 10 μM peptide 206, peptide 218 O, or peptide 218 N prior to Evans blue evaluation. The brain content of Evans blue was quantified by absorbance at 620 nm.

Figure 5:
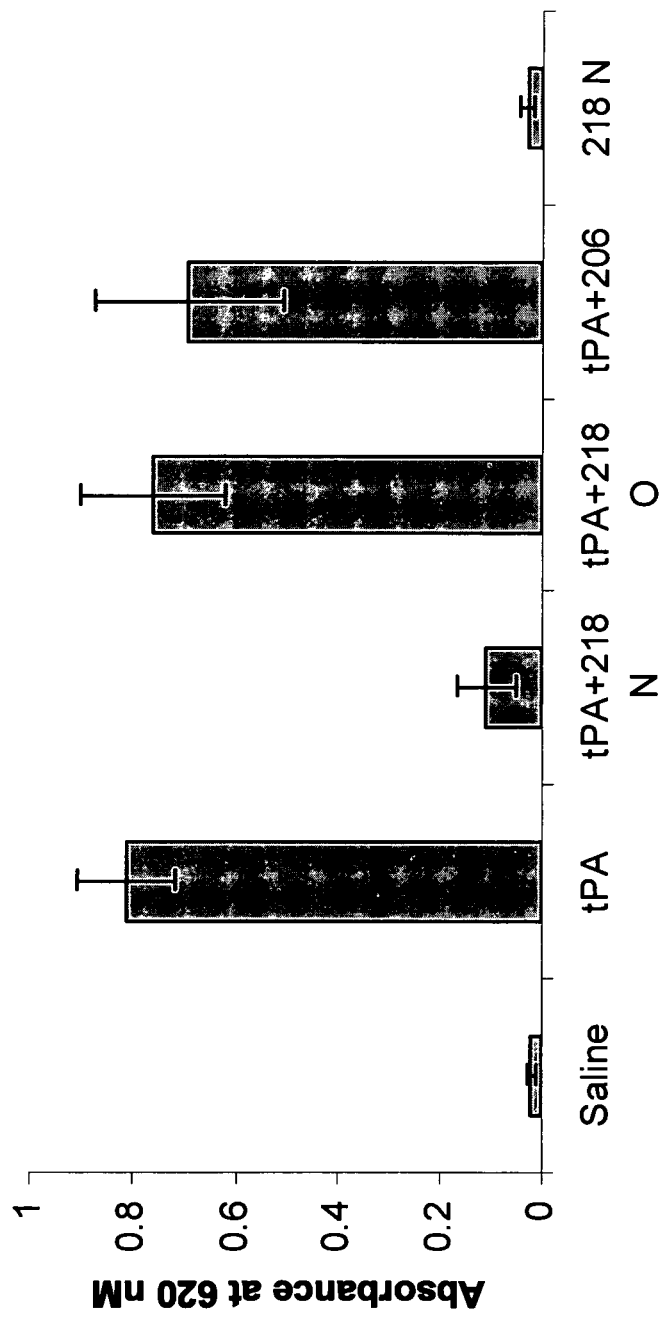
FIG. 5 shows the effect of peptide 206, peptide 218 O, and peptide 218 N on tPA-induced opening of the brain blood barrier (BBB) in mice.

FIG. 5 shows that tPA dramatically increased the BBB permeability. The addition of peptide 218 N to tPA prevented about 90% of this loss of BBB integrity, while peptides 206 or 218 O had no effect. Without wishing to be bound to a specific mechanism or theory, the capability of peptide 218 N to prevent the deleterious effect of tPA on the BBB may be attributed to conformational changes imposed by the peptide on tPA.

Example 4

Effect of PM-1 Derived Peptides on tPA Related Mortality

The effect of the PAI-1 derived peptides on mortality after transient mechanical obstruction of the MCA in rats treated with tPA was examined. tPA injected intravenously two hours after establishing reperfusion increased the mortality rate from 7.7% in the control group treated with saline alone, to 28.6% (p=0.029) (FIG. 6).

Figure 6A:
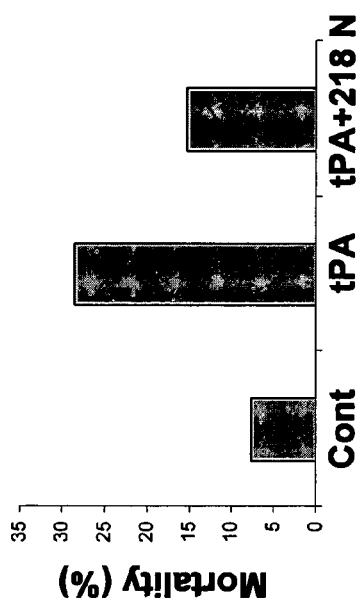
FIGS. 6A-B show the effect of peptide 218 N on the tPA associated post mechanical stroke mortality.

Co-injection of tPA with peptide 218 N significantly reduced the absolute mortality, which dropped from 28.6% to 15.4% (FIG. 6A).

Figure 6B:
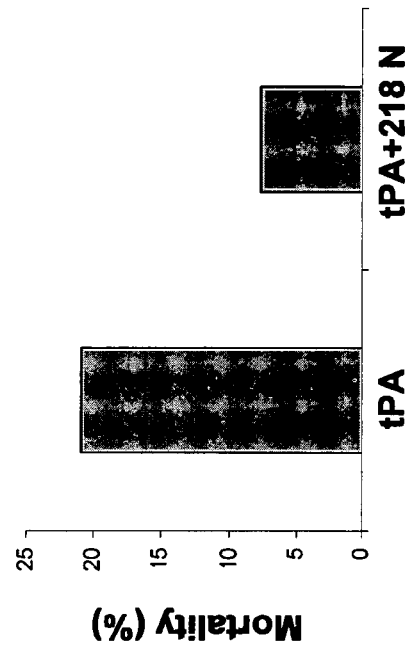

Furthermore, our data showed that the peptide 218 N reduced the tPA associated increase in mortally by 63% (FIG. 6B).

Table 1 shows the effects of peptide 218 N on mortality and intracranial hemorrhage as compared to those of peptide 218 O.

TABLE 1

Effects of PAI-1 derived peptides on tPA-induced mortality in rats.

|  | Control | tPA | tPA + 218 O | tPA + 218 N |
|---|---|---|---|---|
| Mortality | 1/12 | 6/21 | 7/18 | 1/11 |
| Intracranial hemorrhage | 0 | 3 | 0 | 0 |

As shown in Table 1, tPA induced mortality in 6 out of 21 rats (~29% mortality). While peptide 218 O increased tPA-induced mortality to 39%, peptide 218 N reduced the mortality significantly (9% mortality). In addition, some of the tPA-treated rats exhibited intracranial hemorrhage. However, none of the rats treated with tPA and peptides had such hemorrhage.

Example 5

Effect of PAI-1 Derived Peptides on Brain Infarct

Figure 7:
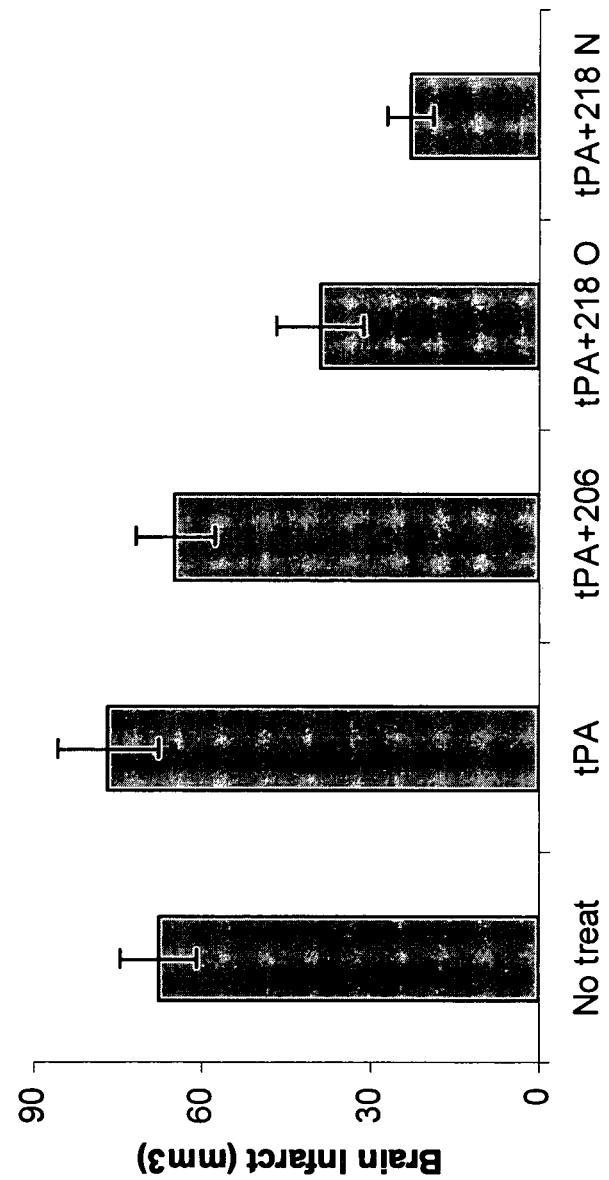
FIG. 7 shows the effect of peptides 206, 218 O, and 218 N on brain infarct in rats treated with tPA together with the peptides four hours after establishing mechanical stroke.

The effect of the PAI-1 derived peptides on infarct size was determined in rats that underwent MCA and reperfusion and four hours later treated with tPA alone or together with PAI-1 derived peptides. tPA injected intravenously four hours after establishing reperfusion increased the infarct size from 68±7 to 77±9 mm3 (FIG. 7). Co-injection of peptide 218 O significantly reduced the infarct size associated with the tPA treatment (FIG. 7) (P<0.01). The effect of the peptide 218 N was significantly stronger than that of 218 O and 206 (P<0.05; FIG. 7). These results indicate that both peptides, and specifically 218 N, improve the therapeutic window of tPA.

Example 6

Effect of PAM Derived Peptides on tPA-Induced Vasoactivity

The effect of tPA alone or tPA together with peptides 218O or 218N on phenylephrine-induced contraction of rat aorta rings in vitro is determined by the procedure described by Haj-Yehia et al., FASEB J. 14:1411-1422 (2000).

Briefly, male Sprague Dawley rats (250-275 g) are killed by exsanguination. The thoracic aortas are removed with care to avoid damage to the endothelium, dissected free of fat and connective tissue, and cut into transverse rings of 5 mm in length. The tissues are kept in an oxygenated (95% $O_2$, 5% $CO_2$) solution of Krebs-Henseliet (KH) buffer. The rings are mounted to record isometric tension in a 10 ml bath containing KH solution under continuous aeration. The rings are equilibrated for 1.5 h at 37° C. and maintained under a resting tension of 2 g throughout the experiment. Each aortic ring is then contracted by adding phenylepherine (PE) in stepwise increments (for 0.1 nM to 10 μM). In other experiments, various concentrations of tPA alone or tPA together with 218O or 218N are added 15 min before adding PE. Isometric tension is measured with a force displacement transducer and recorded online using a computerized system.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

What is claimed is:

1. An isolated peptide having the amino acid sequence as set forth in SEQ ID NO:3:

R$_1$-Arg-Met-Ala-Pro-Glu-Glu-Ile-Ile-Met-Asp-Arg-Pro-Phe-Leu-Phe-Val-Val-Arg R$_2$, wherein R$_1$ is selected from the group consisting of a hydrogen, acetyl, alkyl, and an amino blocking group; and R$_2$ is selected from the group consisting of a carboxyl, amide, ester, and a carboxyl blocking group.

2. The peptide according to claim 1 which has the amino acid sequence set forth in SEQ ID NOs:1, 4, 5 or 6.

3. The peptide according to claim 1 which has the amino acid sequence set forth in SEQ ID NO:1.

4. A pharmaceutical composition comprising an isolated peptide which has the amino acid sequence set forth in SEQ ID NO:3:

R$_1$-Arg-Met-Ala-Pro-Glu-Glu-Ile-Ile-Met-Asp-Arg-Pro-Phe-Leu-Phe-Val-Val-Arg R$_2$, wherein R$_1$ is selected from the group consisting of a hydrogen, acetyl, alkyl, and an amino blocking group; and R$_2$ is selected from the group consisting of a carboxyl, amide, ester, and a carboxyl blocking group, the pharmaceutical composition further comprising a pharmaceutically acceptable carrier.

5. The pharmaceutical composition according to claim 4, wherein the peptide has the amino acid sequence set forth in SEQ ID NOs:1, 4, 5 or 6.

6. The pharmaceutical composition according to claim 4, wherein the peptide has the amino acid sequence set forth in SEQ ID NO:1.

7. A method for reducing neurological damage attributed to a stroke, traumatic brain injury, or ischemic brain injury in a subject comprising administering to the subject a pharmaceutical composition comprising a therapeutically effective amount of an isolated peptide which has the amino acid sequence set forth in SEQ ID NO:3:

R$_1$-Arg-Met-Ala-Pro-Glu-Glu-Ile-Ile-Met-Asp-Arg-Pro-Phe-Leu-Phe-Val-Val-Arg-R$_2$, wherein R$_1$ is selected from the group consisting of a hydrogen, acetyl, alkyl, and an amino blocking group; and R$_2$ is selected from the group consisting of a carboxyl, amide, ester, and a carboxyl blocking group, the pharmaceutical composition further comprising a pharmaceutically acceptable carrier.

8. The method according to claim 7, wherein the peptide has the amino acid sequence set forth in SEQ ID NOs:1, 4, 5, or 6.

9. The method according to claim 7, wherein the peptide has the amino acid sequence set forth in SEQ ID NO:1.

10. The method according to claim 7, wherein the pharmaceutical composition is administered by intravenous, subcutaneous, intramuscular, intraperitoneal, oral, topical, intradermal, transdermal, intranasal, epidural, ophthalmic, vaginal or rectal administration route.

11. The method according to claim 7, wherein the pharmaceutical composition further comprises a therapeutically effective amount of a fibrinolytic agent.

12. The method according to claim 11, wherein the fibrinolytic agent is selected from the group consisting of tPA, uPA, scuPA, tcuPA, streptokinase, rt-PA, alteplase, reteplase, lanoteplase, TNK-rt-PA, anisoylated plasminogen streptokinase complex, anistreplase, and derivatives thereof.

13. The method according to claim 11, wherein the isolated peptide or fragment thereof is administered after administration of the fibrinolytic agent.

14. A method of fibrinolytic therapy comprising administering to a subject in need thereof a pharmaceutical composition comprising a therapeutically effective amount of a fibrinolytic agent and an isolated peptide which has the amino acid sequence as set forth in SEQ ID NO:3:

$R_1$-Arg-Met-Ala-Pro-Glu-Glu-Ile-Ile-Met-Asp-Arg-Pro-Phe-Leu-Phe-Val-Val-Arg-$R_2$, wherein $R_1$ is selected from the group consisting of a hydrogen, acetyl, alkyl, and an amino blocking group; and $R_2$ is selected from the group consisting of a carboxyl, amide, ester, and a carboxyl blocking group, the pharmaceutical composition further comprising a pharmaceutically acceptable carrier.

15. The method according to claim 14, wherein the peptide has the amino acid sequence set forth in SEQ ID NOs: 4, 5, or 6.

16. The method according to claim 14, wherein the peptide has the amino acid sequence set forth in SEQ ID NO:1.

17. The method according to claim 14, wherein the fibrinolytic agent is selected from the group consisting of tPA, uPA, scuPA, tcuPA, streptokinase, rt-PA, alteplase, reteplase, lanoteplase, TNK-rt-PA, anisoylated plasminogen streptokinase complex, anistreplase, and derivatives thereof.

18. The method according to claim 14, wherein the pharmaceutical composition is administered by intravenous, subcutaneous, intramuscular, intraperitoneal, oral, topical, intradermal, transdermal, intranasal, epidural, ophthalmic, vaginal or rectal administration route.

19. The method according to claim 14, wherein the peptide is administered after administration of the fibrinolytic agent.

* * * * *

UNITED STATES PATENT AND TRADEMARK OFFICE
CERTIFICATE OF CORRECTION

PATENT NO. : 8,507,436 B2
APPLICATION NO. : 12/670099
DATED : August 13, 2013
INVENTOR(S) : Higazi It is certified that error appears in the above-identified patent and that said Letters Patent is hereby corrected as shown below:

In the Claims

Column 29;
Line 23 (claim 13, line 2), after "peptide" delete "or fragment thereof".

Signed and Sealed this
Twenty-fourth Day of September, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,507,436 B2  
APPLICATION NO. : 12/670099  
DATED : August 13, 2013  
INVENTOR(S) : Higazi Page 1 of 1

It is certified that error appears in the above-identified patent and that said Letters Patent is hereby corrected as shown below:

In the Claims

Column 30:
Line 11 (claim 15, line 2), after "SEQ ID NOS:" and before "4," insert -- 1, --.

Signed and Sealed this  
Nineteenth Day of November, 2013

Teresa Stanek Rea  
*Deputy Director of the United States Patent and Trademark Office*

UNITED STATES PATENT AND TRADEMARK OFFICE
CERTIFICATE OF CORRECTION

PATENT NO.        : 8,507,436 B2                          Page 1 of 1
APPLICATION NO.   : 12/670099
DATED             : August 13, 2013
INVENTOR(S)       : Abd Al-Roof Higazi It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 696 days.

Signed and Sealed this

Fifteenth Day of September, 2015

Michelle K. Lee
*Director of the United States Patent and Trademark Office*

SEQUENCE LISTING

<160> NUMBER OF SEQ ID NOS: 12

<210> SEQ ID NO 1
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)

```
<223> OTHER INFORMATION: aetyl-Arg
<220> FEATURE:
<221> NAME/KEY: MISC_FEATURE
<222> LOCATION: (18)..(18)
<223> OTHER INFORMATION: Arg-amide

<400> SEQUENCE: 1

Xaa Met Ala Pro Glu Glu Ile Ile Met Asp Arg Pro Phe Leu Phe Val
1               5                   10                  15

Val Xaa

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: acetyl-Arg
<220> FEATURE:
<221> NAME/KEY: MISC_FEATURE
<222> LOCATION: (18)..(18)
<223> OTHER INFORMATION: Arg-amide

<400> SEQUENCE: 2

Xaa Met Ala Pro Glu Glu Ile Ile Met Asp Arg Pro Phe Leu Tyr Val
1               5                   10                  15

Val Xaa

<210> SEQ ID NO 3
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Arg, acetyl-Arg, alkyl-Arg, or amino terminal
      blocked Arg
<220> FEATURE:
<221> NAME/KEY: MISC_FEATURE
<222> LOCATION: (18)..(18)
<223> OTHER INFORMATION: Arg, Arg-amide, Arg-alcohol, Arg-ester, or
      carboxyl blocked Arg

<400> SEQUENCE: 3

Xaa Met Ala Pro Glu Glu Ile Ile Met Asp Arg Pro Phe Leu Phe Val
1               5                   10                  15

Val Xaa

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide

<400> SEQUENCE: 4

Arg Met Ala Pro Glu Glu Ile Ile Met Asp Arg Pro Phe Leu Phe Val
1               5                   10                  15

Val Arg

<210> SEQ ID NO 5
<211> LENGTH: 18
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Acetyl-Arg

<400> SEQUENCE: 5

Xaa Met Ala Pro Glu Glu Ile Ile Met Asp Arg Pro Phe Leu Phe Val
1               5                   10                  15

Val Arg

<210> SEQ ID NO 6
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (18)..(18)
<223> OTHER INFORMATION: Arg-amide

<400> SEQUENCE: 6

Arg Met Ala Pro Glu Glu Ile Ile Met Asp Arg Pro Phe Leu Phe Val
1               5                   10                  15

Val Xaa

<210> SEQ ID NO 7
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Arg, acetyl-Arg, alklyl-Arg, amino blocked Arg
<220> FEATURE:
<221> NAME/KEY: MISC_FEATURE
<222> LOCATION: (15)..(15)
<223> OTHER INFORMATION: Phe or Tyr
<220> FEATURE:
<221> NAME/KEY: MISC_FEATURE
<222> LOCATION: (18)..(18)
<223> OTHER INFORMATION: Arg, Arg-amide, Arg-alcohol, Arg-ester,
      carboxyl blocked Arg

<400> SEQUENCE: 7

Xaa Met Ala Pro Glu Glu Ile Ile Met Asp Arg Pro Phe Leu Xaa Val
1               5                   10                  15

Val Xaa

<210> SEQ ID NO 8
<211> LENGTH: 18
<212> TYPE: PRT
<213> ORGANISM: Artificial Sequence
<220> FEATURE:
<223> OTHER INFORMATION: Synthetic peptide

<400> SEQUENCE: 8

Arg Met Ala Pro Glu Glu Ile Ile Met Asp Arg Pro Phe Leu Tyr Val
1               5                   10                  15

Val Arg

<210> SEQ ID NO 9
<211> LENGTH: 18
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Acetyl-Arg

<400> SEQUENCE: 9

Xaa Met Ala Pro Glu Glu Ile Ile Met Asp Arg Pro Phe Leu Tyr Val
1               5                   10                  15

Val Arg

<210> SEQ ID NO 10
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (18)..(18)
<223> OTHER INFORMATION: Arg-amide

<400> SEQUENCE: 10

Arg Met Ala Pro Glu Glu Ile Ile Met Asp Arg Pro Phe Leu Tyr Val
1               5                   10                  15

Val Xaa

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Glu Glu Ile Ile Met Asp
1               5

<210> SEQ ID NO 12
<211> LENGTH: 402
<212> TYPE: PRT
<213> ORGANISM: Homo sapiens

<400> SEQUENCE: 12

Met Gln Met Ser Pro Ala Leu Thr Cys Leu Val Leu Gly Leu Ala Leu
1               5                   10                  15

Val Phe Gly Glu Gly Ser Ala Val His His Pro Pro Ser Tyr Val Ala
                20                  25                  30

His Leu Ala Ser Asp Phe Gly Val Arg Val Phe Gln Gln Val Ala Gln
            35                  40                  45

Ala Ser Lys Asp Arg Asn Leu Val Phe Ser Pro Tyr Gly Val Ala Ser
        50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
                100                 105                 110

Glu Ile Ser Thr Thr Asp Ala Ile Phe Val Gln Arg Asp Leu Lys Leu
            115                 120                 125
```

```
                            -continued

Val Gln Gly Phe Met Pro His Phe Arg Leu Phe Arg Ser Thr Val
    130             135             140

Lys Gln Val Asp Phe Ser Glu Val Glu Arg Ala Arg Phe Ile Ile Asn
145             150             155             160

Asp Trp Val Lys Thr His Thr Lys Gly Met Ile Ser Asn Leu Leu Gly
                165             170             175

Lys Gly Ala Val Asp Gln Leu Thr Arg Leu Val Leu Val Asn Ala Leu
            180             185             190

Tyr Phe Asn Gly Gln Trp Lys Thr Pro Phe Pro Asp Ser Ser Thr His
        195             200             205

Arg Arg Leu Phe His Lys Ser Asp Gly Ser Thr Val Ser Val Pro Met
    210             215             220

Met Ala Gln Thr Asn Lys Phe Asn Tyr Thr Glu Phe Thr Thr Pro Asp
225             230             235             240

Gly His Tyr Tyr Asp Ile Leu Glu Leu Pro Tyr His Gly Asp Thr Leu
                245             250             255

Ser Met Phe Ile Ala Ala Pro Tyr Glu Lys Glu Val Pro Leu Ser Ala
            260             265             270

Leu Thr Asn Ile Leu Ser Ala Gln Leu Ile Ser His Trp Lys Gly Asn
        275             280             285

Met Thr Arg Leu Pro Arg Leu Leu Val Leu Pro Lys Phe Ser Leu Glu
    290             295             300

Thr Glu Val Asp Leu Arg Lys Pro Leu Glu Asn Leu Gly Met Thr Asp
305             310             315             320

Met Phe Arg Gln Phe Gln Ala Asp Phe Thr Ser Leu Ser Asp Gln Glu
                325             330             335

Pro Leu His Val Ala Gln Ala Leu Gln Lys Val Lys Ile Glu Val Asn
            340             345             350

Glu Ser Gly Thr Val Ala Ser Ser Ser Thr Ala Val Ile Val Ser Ala
        355             360             365

Arg Met Ala Pro Glu Glu Ile Ile Met Asp Arg Pro Phe Leu Phe Val
    370             375             380

Val Arg His Asn Pro Thr Gly Thr Val Leu Phe Met Gly Gln Val Met
385             390             395             400

Glu Pro
```